United States Patent
Gyoten et al.

(10) Patent No.: US 11,471,575 B2
(45) Date of Patent: Oct. 18, 2022

(54) HEAT EXCHANGER AND OXYGENATOR

(71) Applicant: TERUMO KABUSHIKI KAISHA, Tokyo (JP)

(72) Inventors: Akira Gyoten, Elkton, MD (US); Wataru Matsumoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 680 days.

(21) Appl. No.: 16/513,793

(22) Filed: Jul. 17, 2019

(65) Prior Publication Data
US 2019/0336668 A1    Nov. 7, 2019

Related U.S. Application Data

(63) Continuation of application No. PCT/JP2018/001374, filed on Jan. 18, 2018.

(30) Foreign Application Priority Data

Jan. 26, 2017    (JP) .............................. JP2017-012543

(51) Int. Cl.
*A61M 1/16* (2006.01)
*A61M 60/113* (2021.01)
*A61M 60/205* (2021.01)

(52) U.S. Cl.
CPC ........ *A61M 1/1629* (2014.02); *A61M 1/1698* (2013.01); *A61M 60/113* (2021.01); *A61M 60/205* (2021.01)

(58) Field of Classification Search
CPC .............. A61M 1/1629; A61M 1/1698; A61M 60/113; A61M 60/205; A61M 2205/366; B01D 63/02; B01D 63/026; B01D 67/0088; B01D 71/56; B01D 2325/20
See application file for complete search history.

(56) References Cited

U.S. PATENT DOCUMENTS

| | | | |
|---|---|---|---|
| 4,791,054 A | | 12/1988 | Hamada et al. |
| 4,879,043 A | * | 11/1989 | Boughton ............ B01D 61/025 210/651 |
| 2005/0255019 A1 | * | 11/2005 | Parrish ................... B01D 53/56 422/177 |

(Continued)

FOREIGN PATENT DOCUMENTS

| | | |
|---|---|---|
| CN | 101663057 A | 3/2010 |
| JP | 06096098 B | 3/1990 |

(Continued)

OTHER PUBLICATIONS

European Search Report, EP18745409.05, dated Mar. 22, 2021.
(Continued)

*Primary Examiner* — Benjamin J Klein
(74) *Attorney, Agent, or Firm* — MacMillan, Sobanski & Todd, LLC

(57) ABSTRACT

A heat exchanger for a blood circulation circuit includes a hollow fiber membrane layer having a plurality of laminated hollow fiber membranes 31. Each of the hollow fiber membranes 31 has a barrier layer 5 having a hydrogen peroxide barrier property, and the barrier layer 5 has an oxygen permeability coefficient of 6 cc·cm/m²·24 h/atm or less at 25° C.

20 Claims, 11 Drawing Sheets

(56) References Cited

U.S. PATENT DOCUMENTS

| | | | |
|---|---|---|---|
| 2007/0199891 A1* | 8/2007 | Mabuchi | D01D 5/24 264/41 |
| 2008/0000830 A1* | 1/2008 | Mabuchi | B01D 67/009 210/500.23 |
| 2010/0076082 A1* | 3/2010 | Gamet | C11D 3/2079 514/557 |
| 2016/0331882 A1* | 11/2016 | Saito | A61M 1/1629 |

FOREIGN PATENT DOCUMENTS

| | | |
|---|---|---|
| JP | 10263375 A | 10/1998 |
| JP | 2005270622 A | 10/2005 |
| JP | 2010046587 A | 3/2010 |

OTHER PUBLICATIONS

International Search Report, PCT/JP2018/001374, dated Jun. 3, 2018.
Written Opinion of the International Searching Authority, PCT/JP2018/001374, dated Jan. 18, 2018, Terumo Kabushiki Kaisha, dated Mar. 6, 2018.
Chinese Office Action, 201880005254, dated Aug. 4, 2021.

* cited by examiner

HEAT EXCHANGER AND OXYGENATOR

CROSS REFERENCE TO RELATED APPLICATIONS

This application is a continuation of PCT Application No. PCT/JP2018/001374, filed Jan. 18, 2018, based on and claiming priority to Japanese Application No. 2017-012543, filed Jan. 26, 2017, both of which are incorporated herein by reference in their entirety.

BACKGROUND OF THE INVENTION

The present invention relates to a heat exchanger and an oxygenator.

In the related art, a heat exchanger and an oxygenator having a hollow fiber membrane bundle which is constituted of a large number of hollow fiber membranes and which has a cylindrical shape as a whole are known. In this hollow fiber membrane bundle having a cylindrical shape, a hollow fiber membrane sheet as disclosed in U.S. Pat. No. 4,911,846 can be applied. In U.S. Pat. No. 4,911,846, a large number of hollow fiber membranes are disposed substantially in parallel so as to be weft strings, and these are woven together with warp strings, thereby forming a bamboo blind-shaped sheet. Such a bamboo blind-shaped hollow fiber membrane sheet can be folded to form a hollow fiber membrane bundle having a prismatic outer shape, or a hollow fiber membrane bundle having a columnar shape.

In a case where the hollow fiber membrane bundle as described above is used as a heat exchanger, a heat medium is circulated inside the hollow fiber membranes, and blood is circulated outside the hollow fiber membranes. Accordingly, the temperature of blood can be adjusted through the hollow fiber membranes.

Here, in recent years, a liquid containing hydrogen peroxide solution is circulated as a heat medium inside the hollow fiber membranes. Accordingly, sterilization of a cold water tank which adjusts the temperature of the heat medium can be performed. However, depending on the constituent material of the hollow fiber membrane, hydrogen peroxide in the hydrogen peroxide solution may penetrate, resulting an increase in the concentration of hydrogen peroxide in the blood.

SUMMARY OF THE INVENTION

An object of the present invention is to provide a heat exchanger and an oxygenator capable of preventing hydrogen peroxide from permeating into blood even in a case where a liquid containing hydrogen peroxide solution is used as a heat medium.

A heat exchanger for achieving the above object includes a hollow fiber membrane layer having a plurality of hollow fiber membranes. Each of the hollow fiber membranes has a barrier layer having a hydrogen peroxide barrier property, and the barrier layer has an oxygen permeability coefficient of 6 cc·cm/m$^2$·24 h/atm or less at 25° C.

The barrier layer is preferably comprised of a crystalline resin material.

The crystalline resin material preferably contains an aliphatic polyamide.

The aliphatic polyamide is comprised of at least one of polyamide 11, polyamide 12, polyamide 10-10, and polyamide 10-12.

When the number of carbon atoms in amide groups of a molecule of the aliphatic polyamide is N and the number of carbon atoms in methylene groups of the aliphatic polyamide is n, then n/N is 9 or larger.

The hollow fiber membrane further has a heat conductive layer having a thermal conductivity higher than that of the barrier layer, and the barrier layer and the heat conductive layer are concentrically laminated.

The heat conductive layer preferably has a thermal conductivity of 0.2 W/m·K or higher and 0.60 W/m·K or lower.

The hollow fiber membrane layer according to one embodiment has a shape of a cylindrical body and has the hollow fiber membranes wound around a central axis of the cylindrical body and inclined with respect to the central axis of the cylindrical body.

The hollow fiber membrane layer may preferably include a formed sheet material having the plurality of hollow fiber membranes braided.

The heat exchanger can preferably be used with a heat medium containing the hydrogen peroxide solution which is allowed to pass through inside the hollow fiber membranes.

A heat exchanger (which can be in an oxygenator) includes a hollow fiber membrane layer having a plurality of hollow fiber membranes. The hollow fiber membranes are formed as a plurality of layers laminated concentrically in a thickness direction of the hollow fiber membranes, and one of the layers is a barrier layer having a hydrogen peroxide barrier property.

According to the present invention, since the barrier layer provided in the hollow fiber membranes has an oxygen permeability coefficient of 6 cc·cm/m$^2$·24 h/atm or less at 25° C., it is possible to prevent hydrogen peroxide from permeating the hollow fiber membranes even in a case where a liquid containing hydrogen peroxide solution is used as a heat medium. Therefore, it is possible to prevent the concentration of hydrogen peroxide in the blood from increasing.

DETAILED DESCRIPTION OF PREFERRED EMBODIMENTS

Hereinafter, a heat exchanger and an oxygenator according to the present invention will be described in detail based on preferred embodiments shown in accompanying drawings.

First Embodiment

Figure 1:
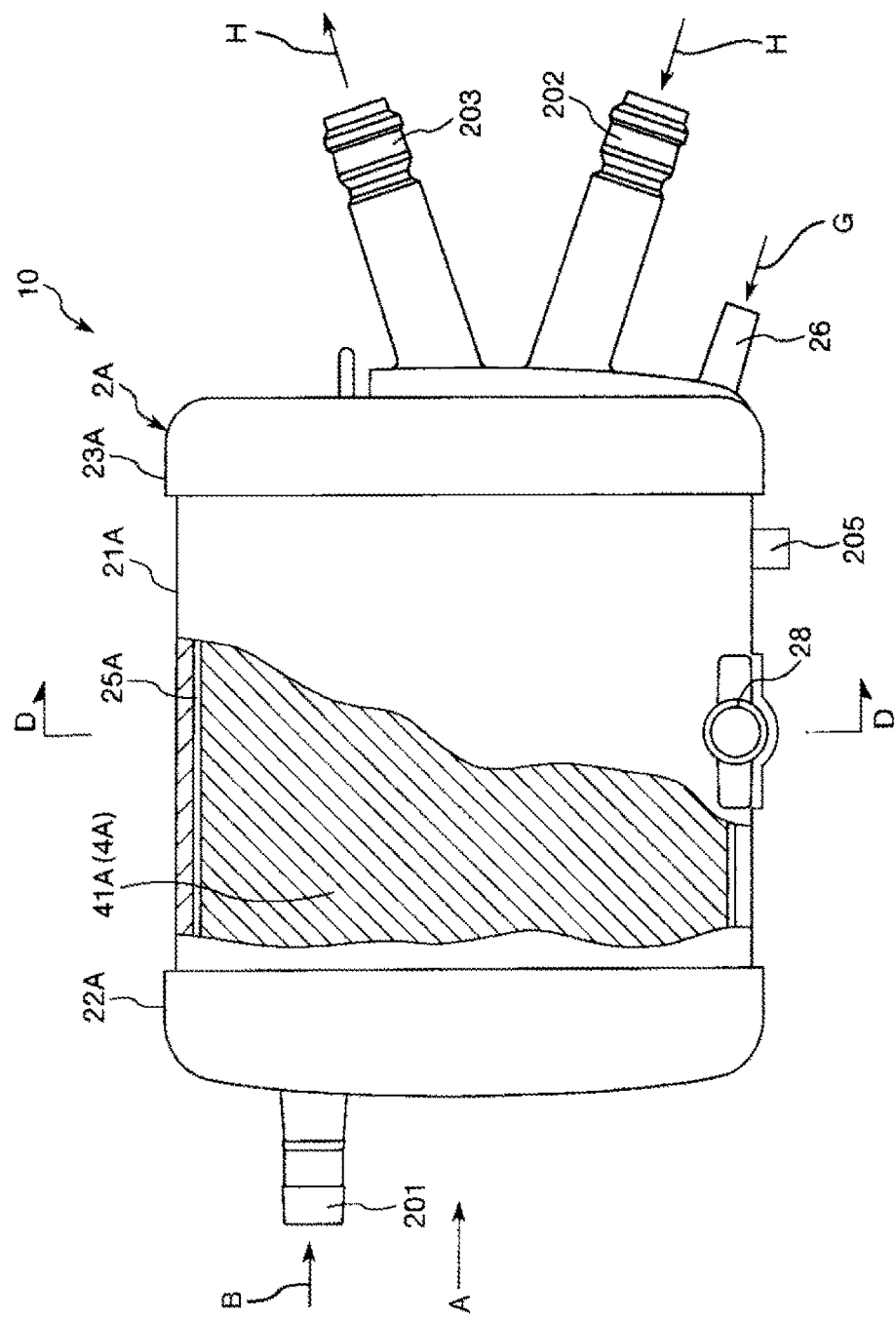
FIG. 1 is a plan view of an oxygenator including a heat exchanger (first embodiment) of the present invention.
Figure 2:
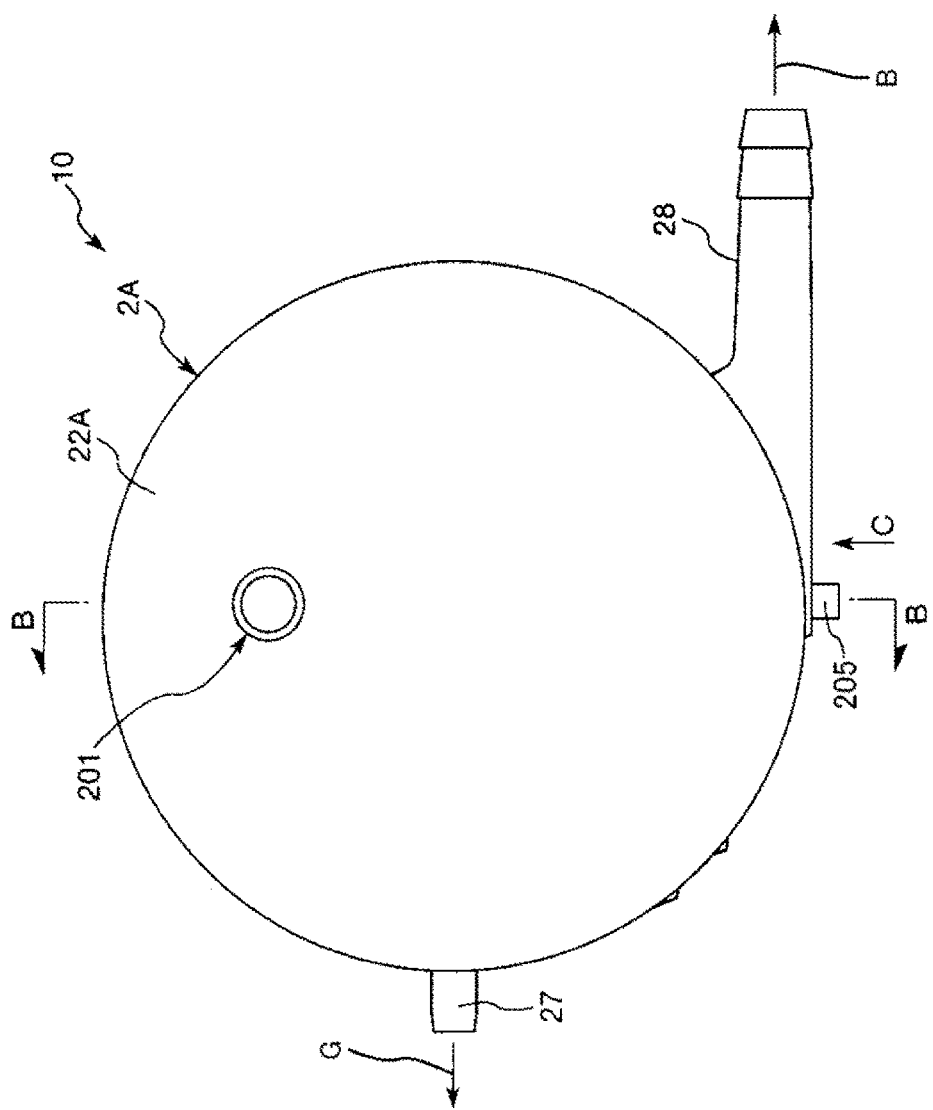
FIG. 2 is a view of the oxygenator shown in FIG. 1 when seen from a direction of arrow A.
Figure 3:
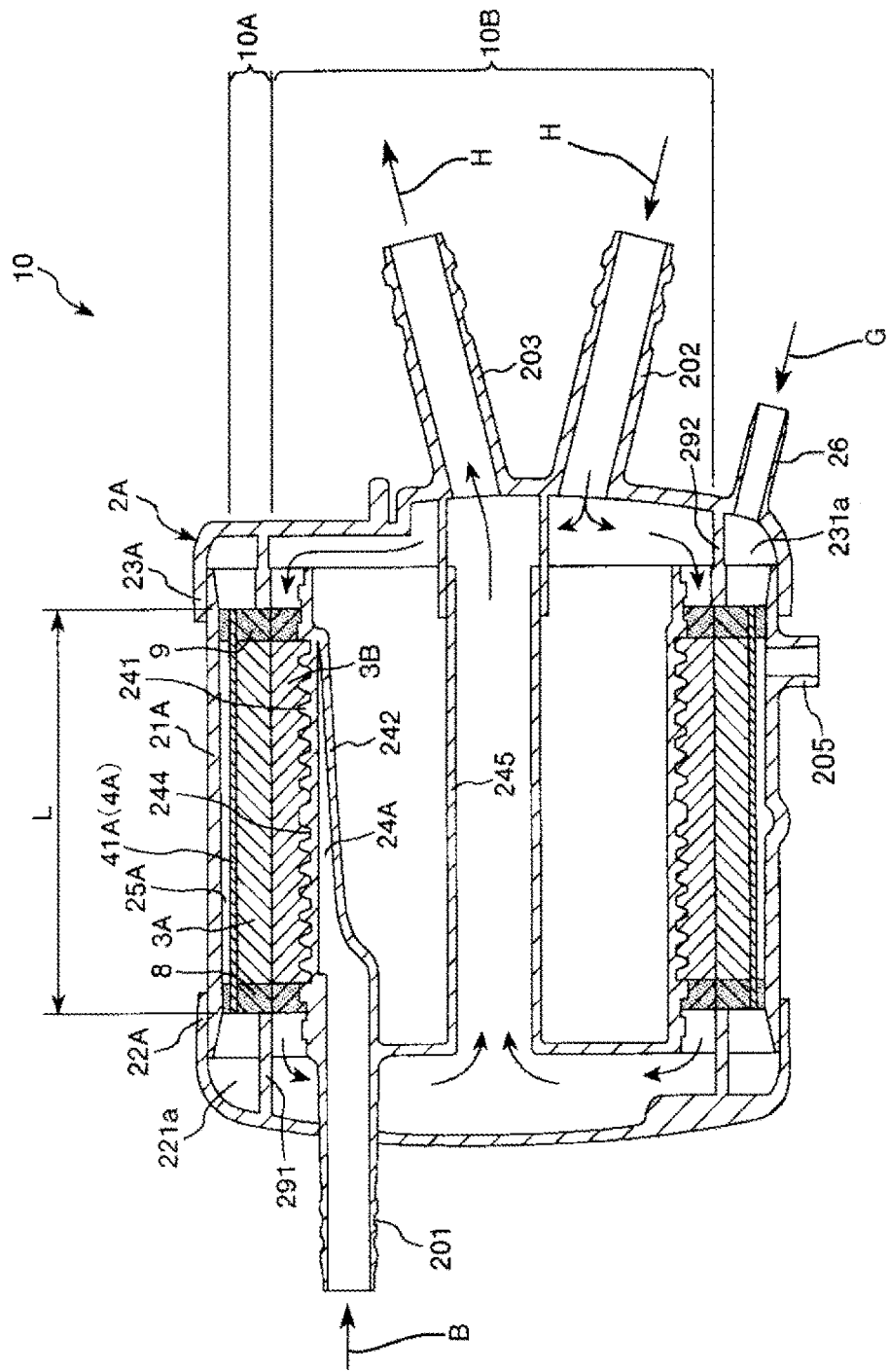
FIG. 3 is a cross-sectional view taken along line B-B in FIG. 2.
Figure 4:
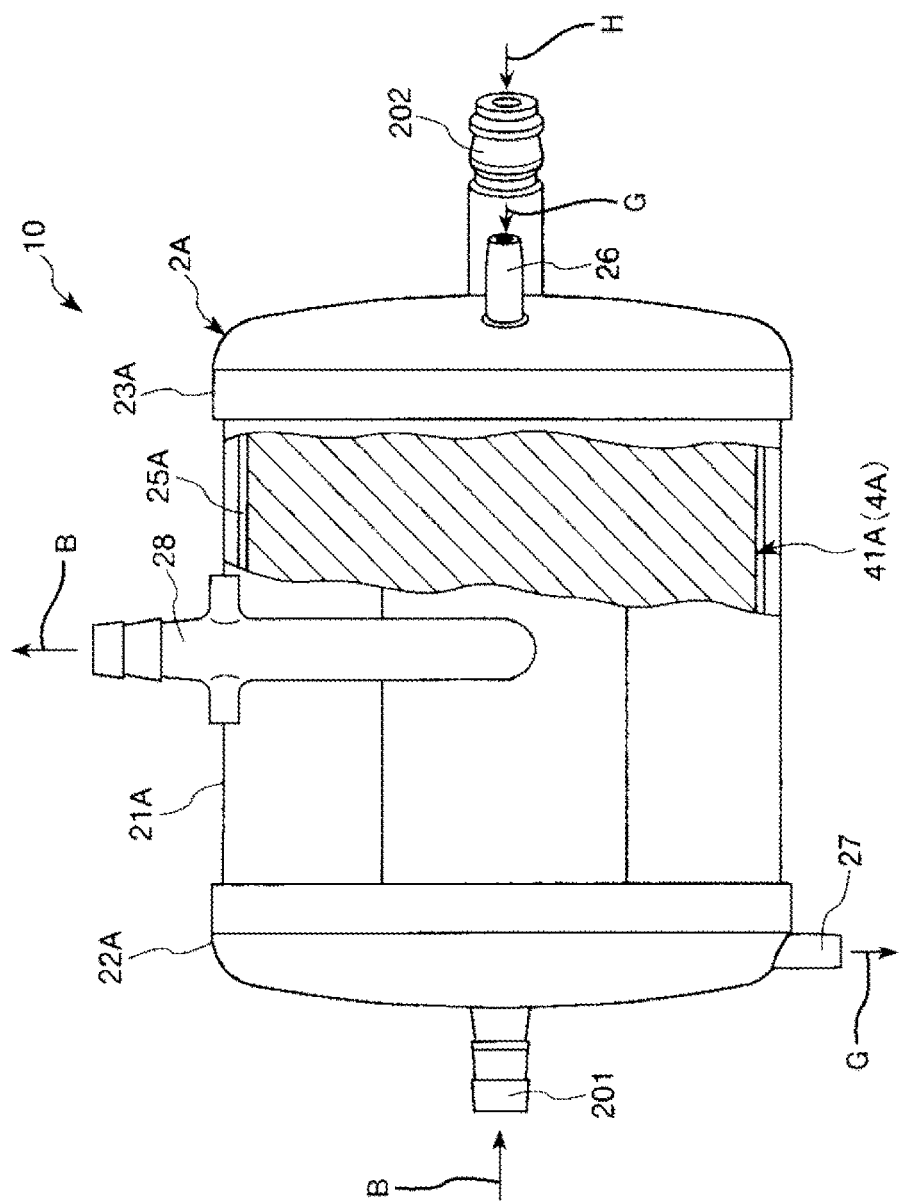
FIG. 4 is a view when seen from a direction of arrow C in FIG. 2.
Figure 5:
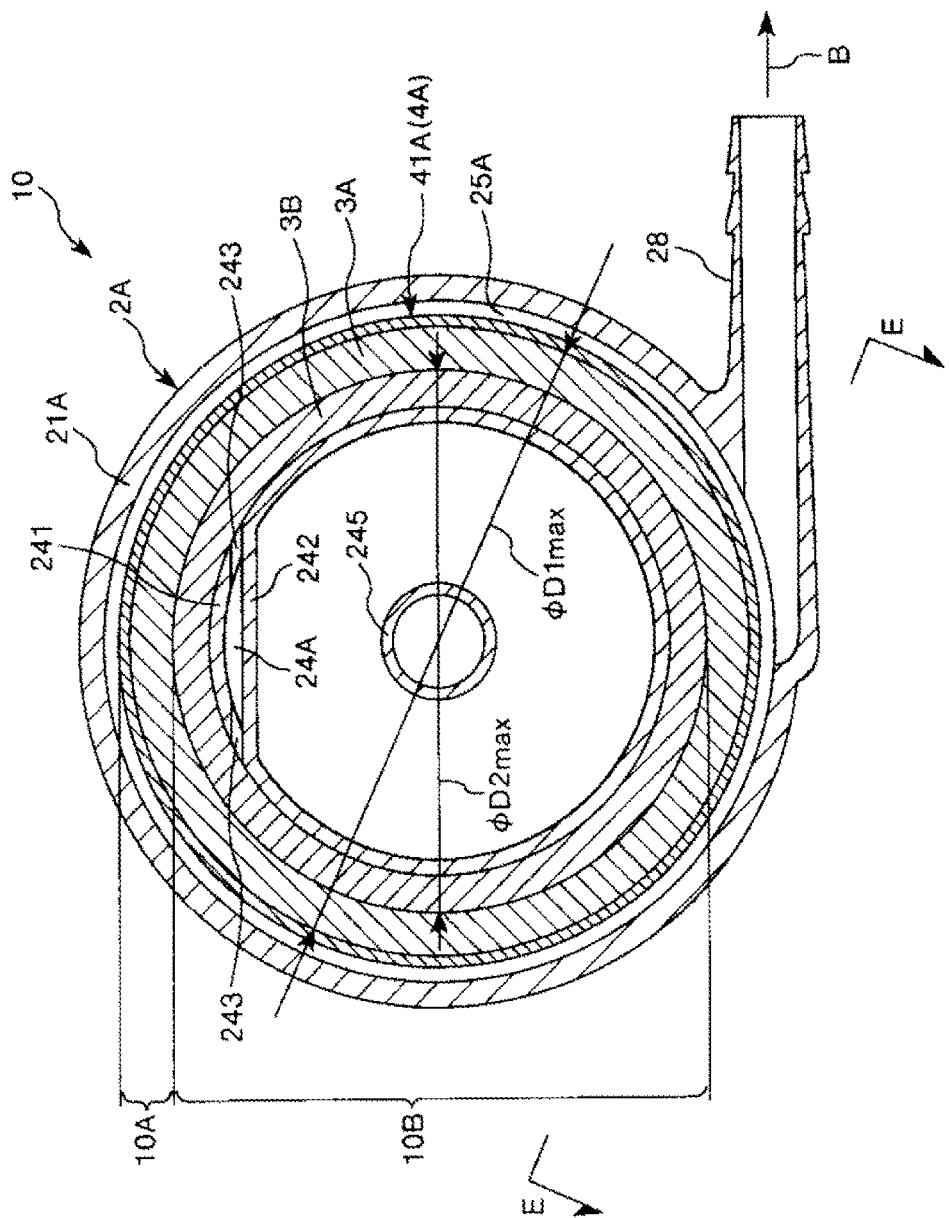
FIG. 5 is a cross-sectional view taken along line D-D in FIG. 1.
Figure 6:
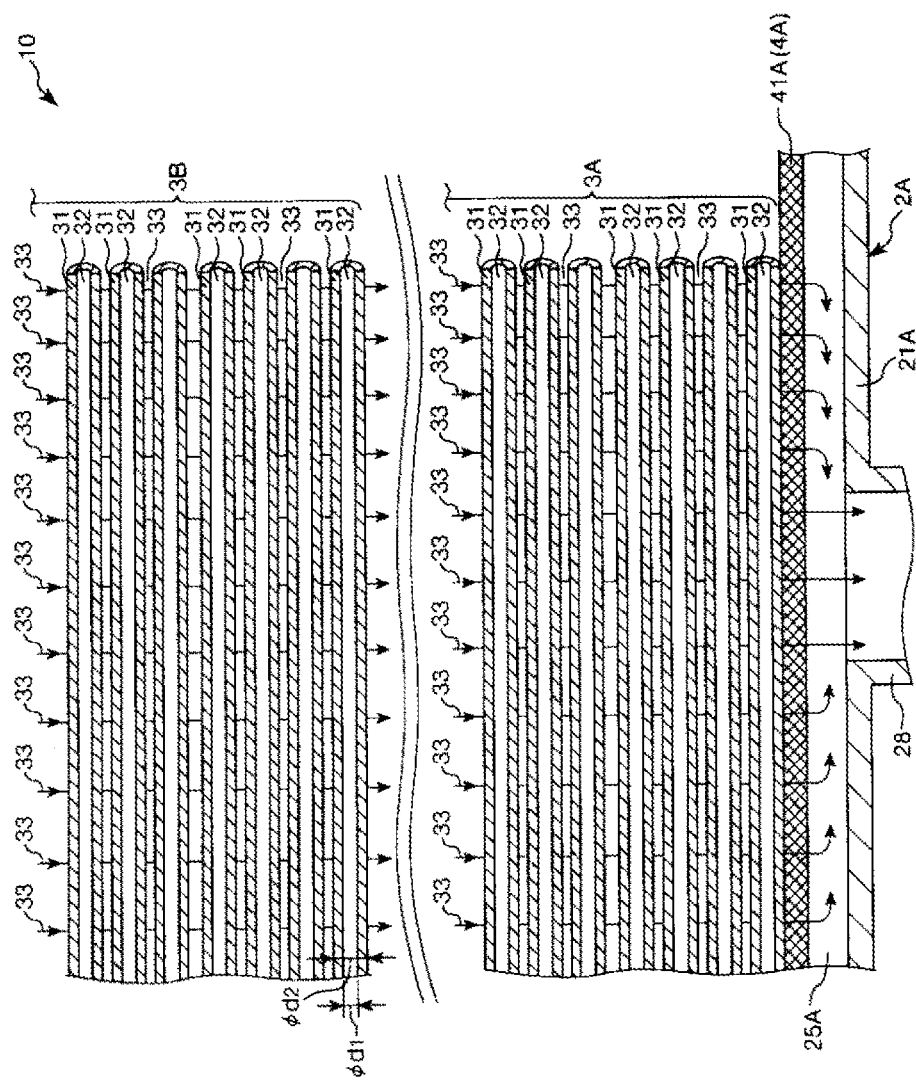
FIG. 6 is a cross-sectional view taken along line E-E in FIG. 5.
Figure 7A:
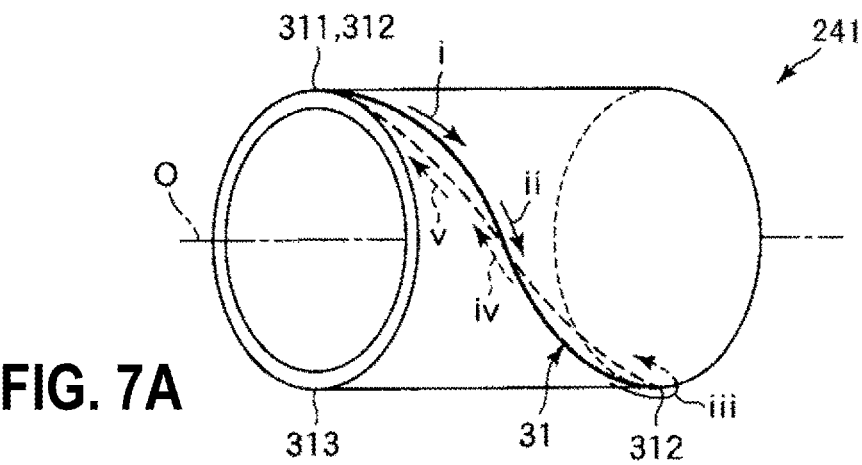
FIG. 7A is a perspective view.
Figure 7B:
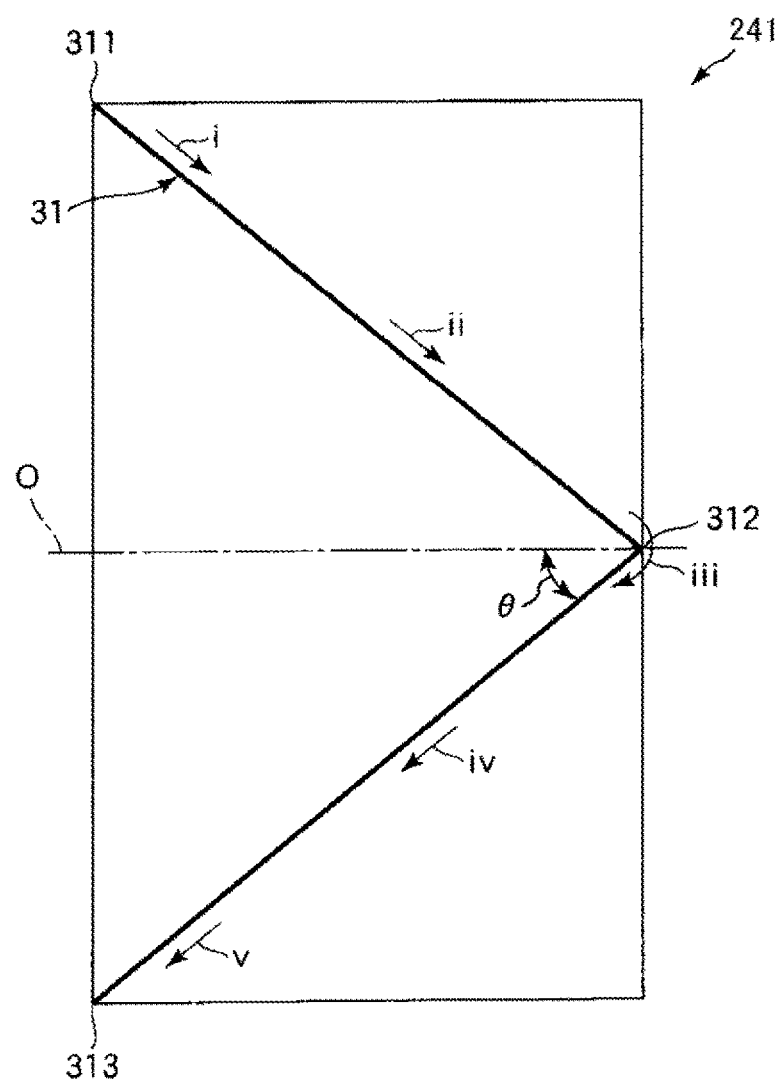
FIG. 7B is a development view showing a process of manufacturing a hollow fiber membrane layer provided in the oxygenator shown in FIG. 1.
Figure 8A:
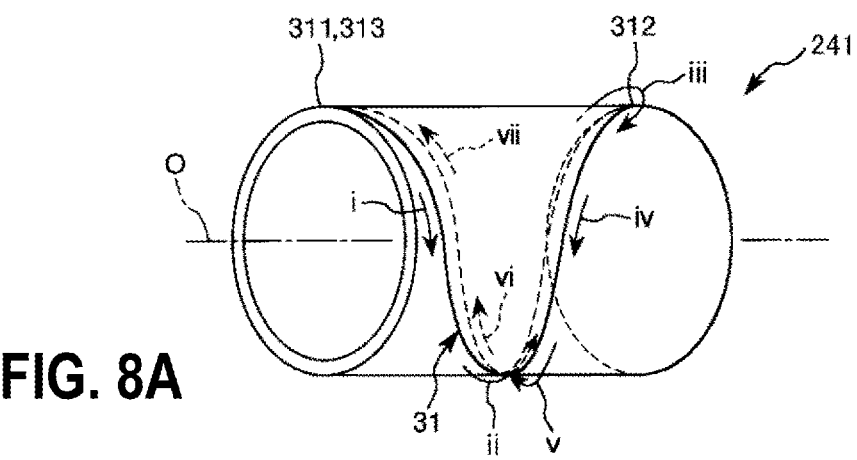
FIG. 8A is a perspective view.
Figure 8B:
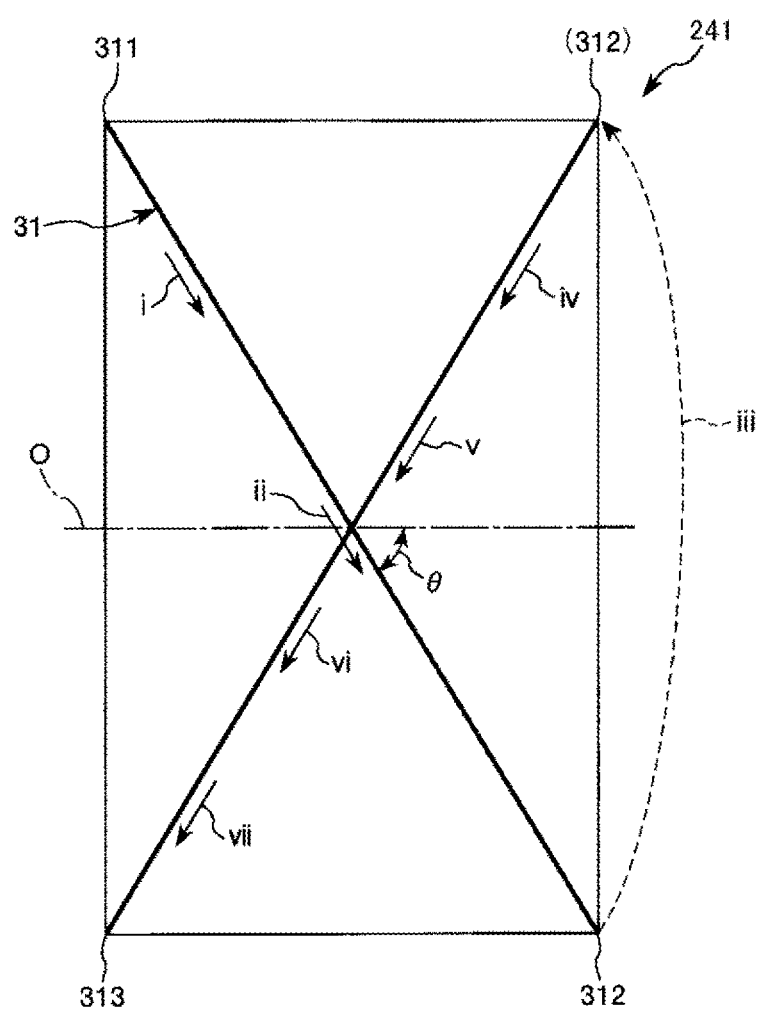
FIG. 8B is a development view showing the process of manufacturing the hollow fiber membrane layer provided in the oxygenator shown in FIG. 1.
Figure 9:
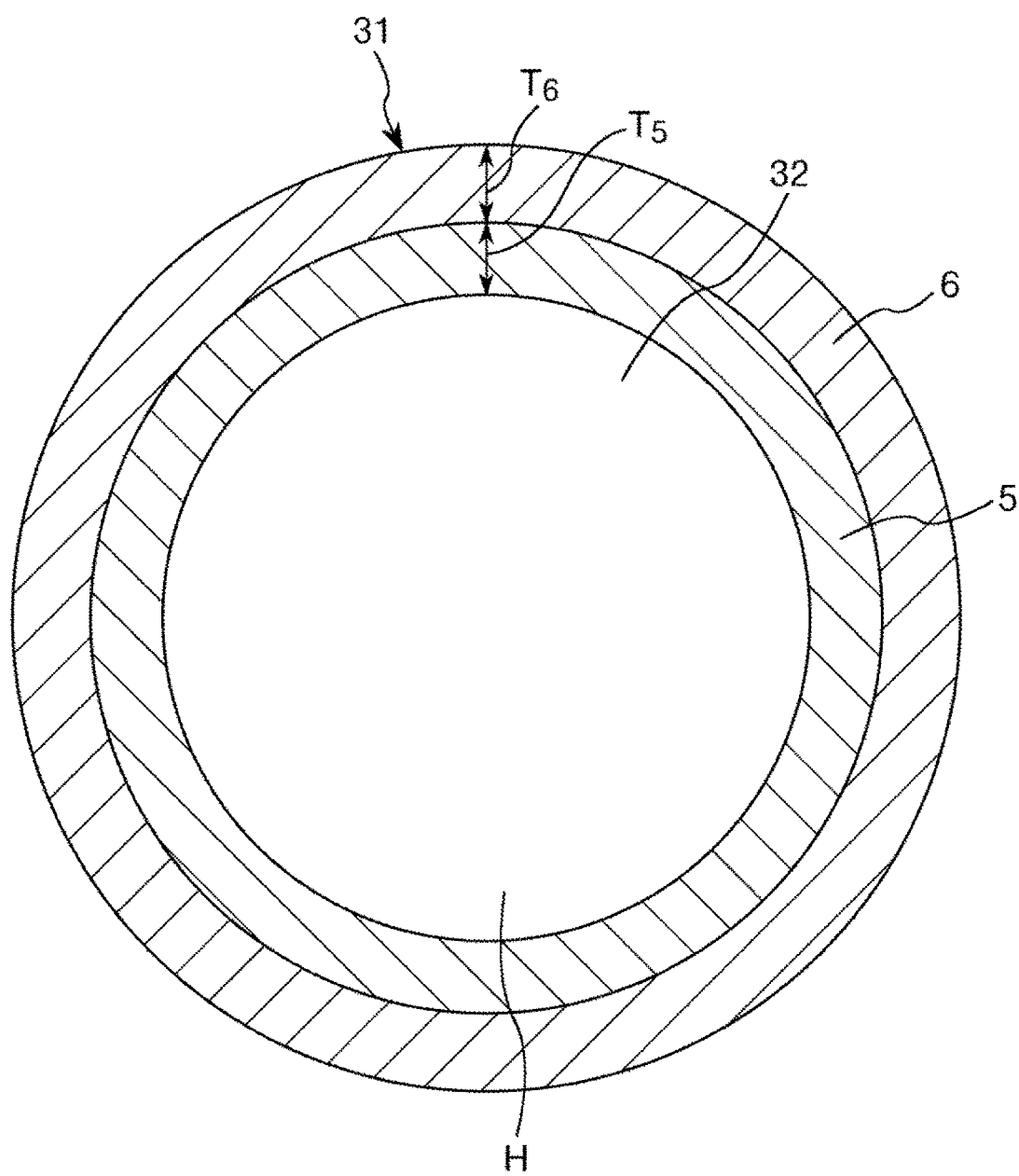
FIG. 9 is a transverse view of a hollow fiber membrane provided in the hollow fiber membrane layer shown in FIG. 1.

FIG. 1 is a plan view of an oxygenator including a heat exchanger according to the present invention (first embodiment). FIG. 2 is a view of the oxygenator shown in FIG. 1 when seen from a direction of arrow A. FIG. 3 is a cross-sectional view taken along line B-B in FIG. 2. FIG. 4 is a view when seen from a direction of arrow C in FIG. 2. FIG. 5 is a cross-sectional view taken along line D-D in FIG. 1. FIG. 6 is a cross-sectional view taken along line E-E in FIG. 5. FIG. 7A is a perspective view, and FIG. 7B is a development view showing a process of manufacturing a hollow fiber membrane layer provided in the oxygenator shown in FIG. 1. FIG. 8A is a perspective view, and FIG. 8B is a development view showing the process of manufacturing the hollow fiber membrane layer provided in the oxygenator shown in FIG. 1. FIG. 9 is a transverse view of a hollow fiber membrane provided in the hollow fiber membrane layer shown in FIG. 1.

Note that, in FIGS. 1, 3, 4, and 7 to 9, the left side is referred to as "left" or a "left portion (one side)" and the right side is referred to as "right" or a "right portion (the other side)". In addition, in FIGS. 1 to 6, the inside of the oxygenator will be described as a "blood inflow side" or an "upstream side" and the outside will be described as a "blood outflow side" or a "downstream side".

The entire shape of an oxygenator 10 shown in FIGS. 1 to 5 is in a substantially columnar shape. This oxygenator 10 is a heat exchanger-attached oxygenator including: a heat exchange portion 10B which is provided inside the oxygenator and performs heat exchange on blood; and an oxygenator portion 10A which is provided on an outer peripheral side of the heat exchange portion 10B and is used as a gas exchange portion performing gas exchange on blood. The oxygenator 10 is installed, for example, in an extracorporeal blood circulation circuit.

The oxygenator 10 has a housing 2A in which the oxygenator portion 10A and the heat exchange portion (heat exchanger) 10B are housed.

The housing 2A includes: a cylindrical housing main body 21A; a dish-like first lid body 22A which seals a left end opening of the cylindrical housing main body 21A; and a dish-like second lid body 23A which seals a right end opening of the cylindrical housing main body 21A.

The cylindrical housing main body 21A, the first lid body 22A, and the second lid body 23A are formed of a resin material. The first lid body 22A and the second lid body 23A are fixed to the cylindrical housing main body 21A through a method such as welding or adhesion using an adhesive.

A tubular blood outlet port 28 is formed on the outer peripheral portion of the cylindrical housing main body 21A. This blood outlet port 28 protrudes toward a substantially tangential direction of the outer peripheral surface of the cylindrical housing main body 21A (refer to FIG. 5).

A tubular purge port 205 is protrusively formed on the outer peripheral portion of the cylindrical housing main body 21A. The purge port 205 is formed on the outer peripheral portion of the cylindrical housing main body 21A such that a central axis of the purge port 205 intersects with a central axis of the cylindrical housing main body 21A.

A tubular gas outlet port 27 is protrusively formed on the first lid body 22A. The gas outlet port 27 is formed on the outer peripheral portion of the first lid body 22A such that a central axis of the first lid body intersects with the center of the first lid body 22A (refer to FIG. 2).

In addition, a blood inlet port 201 protrudes from an end surface of the first lid body 22A such that a central axis of the blood inlet port is eccentric to the center of the first lid body 22A.

A tubular gas inlet port 26, a heat medium inlet port 202, and a heat medium outlet port 203 are protrusively formed on the second lid body 23A. The gas inlet port 26 is formed at an edge portion of the end surface of the second lid body 23A. The heat medium inlet port 202 and the heat medium outlet port 203 are formed at a substantially central portion of the end surface of the second lid body 23A. In addition, central lines of the heat medium inlet port 202 and the heat medium outlet port 203 are slightly inclined to a central line of the second lid body 23A.

Note that, in the present invention, the entire shape of the housing 2A does not necessarily have a complete columnar shape, and may have, for example, a partially missing shape or a shape to which an irregular portion is added.

As shown in FIGS. 3 and 5, the oxygenator portion 10A having a cylindrical shape along the inner peripheral surface of the housing 2A is housed inside the housing 2A. The oxygenator portion 10A includes: a cylindrical hollow fiber membrane layer 3A; and a filter member 41A used as air bubble removing means 4A provided on the outer peripheral side of the hollow fiber membrane layer 3A. The hollow fiber membrane layer 3A and the filter member 41A are disposed in order of the hollow fiber membrane layer 3A and the filter member 41A from a blood inflow side.

In addition, the cylindrical heat exchange portion 10B is provided inside the oxygenator portion 10A and disposed along the inner peripheral surface of the oxygenator portion 10A. The heat exchange portion 10B has the cylindrical hollow fiber membrane layer 3B.

As shown in FIG. 6, each of the hollow fiber membrane layers 3A and 3B includes a plurality of hollow fiber membranes 31, which are laminated in layers. For example, the number of layers laminated is preferably, but not limited to, 3 to 40. Note that each of the hollow fiber membranes 31 in the hollow fiber membrane layer 3A has a gas exchange function. On the other hand, each of the hollow fiber membranes 31 in the hollow fiber membrane layer 3B has a heat exchange function of performing heat exchange.

As shown in FIG. 3, both end portions of the hollow fiber membrane layers 3A and 3B are collectively fixed to the inner surface of the cylindrical housing main body 21A using partition walls 8 and 9. The partition walls 8 and 9 are formed of, for example, potting materials such as polyurethane and silicone rubber, or adhesives. Furthermore, the inner peripheral portion of the hollow fiber membrane layer 3B is engaged with an irregular portion 244 formed on the outer peripheral portion of a first cylindrical member 241. The hollow fiber membrane layer 3B is reliably fixed to the cylindrical housing main body 21A through fixation using the partition walls 8 and 9 and this engagement. Accordingly, it is possible to reliably prevent positional deviation of the hollow fiber membrane layer 3B from occurring during use of the oxygenator 10. In addition, the irregular portion 244 also functions as a flow path for circulating blood B throughout the hollow fiber membrane layer 3B.

Note that, as shown in FIG. 5, the maximum outer diameter $\phi D1_{max}$ of the hollow fiber membrane layer 3A is preferably 20 mm to 200 mm, and more preferably 40 mm to 150 mm. The maximum outer diameter $\phi D2_{max}$ of the hollow fiber membrane layer 3B is preferably 10 mm to 150 mm, and more preferably 20 mm to 100 mm. In addition, as shown in FIG. 3, a length L of the hollow fiber membrane layers 3A and 3A along a central axis direction is preferably 30 mm to 250 mm, and more preferably 50 mm to 200 mm. With such conditions, the hollow fiber membrane layer 3A has an excellent gas exchange function and the hollow fiber membrane layer 3B has an excellent heat exchange function.

A blood flow path 33 through which the blood B flows from the upper side to the lower side in FIG. 6 is formed on the outside of each of the hollow fiber membranes 31 between the partition wall 8 and the partition wall 9 in the housing 2A, that is, in a gap between the hollow fiber membranes 31.

A blood inflow side space 24A communicating with the blood inlet port 201 is formed upstream of the blood flow path 33 as a blood inlet portion of the blood B flowing in from the blood inlet port 201 (refer to FIGS. 3 and 5).

The blood inflow side space 24A is a space defined by the first cylindrical member 241 forming a cylindrical shape and a plate piece 242 which is disposed inside the first cylindrical member 241 and is disposed so as to face a part of the inner peripheral portion of the first cylindrical member. The blood B flowing in the blood inflow side space 24A can flow down throughout blood flow paths 33 through a plurality of side holes 243 formed in the first cylindrical member 241.

In addition, a second cylindrical member 245 concentrically disposed with the first cylindrical member 241 is disposed inside the first cylindrical member 241. As shown in FIG. 3, a heat medium H, for example, water, flowing in from the heat medium inlet port 202 is discharged from the heat medium outlet port 203 after passing through a flow path (hollow portion) 32 in each of the hollow fiber membranes 31 of the hollow fiber membrane layer 3B on the outer peripheral side of the first cylindrical member 241, and the inside of the second cylindrical member 245 in order. In addition, heat exchange (heating or cooling) is performed between the blood B coming into contact with the hollow fiber membranes 31 in the blood flow paths 33 and the heat medium H when the heat medium H passes through the flow path 32 of each of the hollow fiber membranes 31.

The filter member 41A having a function of capturing air bubbles existing in the blood B flowing through the blood flow paths 33 is disposed downstream of the blood flow paths 33.

The filter member 41A is formed of a sheet-like member having a substantially rectangular shape (hereinafter, simply referred to as a "sheet"), and is formed by winding the sheet along the outer periphery of the hollow fiber membrane layer 3A. Both end portions of the filter member 41A are also fixed using the partition walls 8 and 9, and thus, are fixed to the housing 2A (refer to FIG. 3). Note that, it is preferable that the inner peripheral surface of the filter member 41A is provided in contact with the outer peripheral surface of the hollow fiber membrane layer 3A, and covers substantially the entire outer peripheral surface.

In addition, even if there are air bubbles in blood flowing through the blood flow paths 33, the filter member 41A can capture the air bubbles (refer to FIG. 6). In addition, air bubbles captured by the filter member 41A are pushed into each of the hollow fiber membranes 31 in the vicinity of the filter member 41A by blood. As a result, the air bubbles are removed from the blood flow paths 33.

In addition, a cylindrical gap is formed between the outer peripheral surface of the filter member 41A and the inner peripheral surface of the cylindrical housing main body 21A and forms a blood outflow side space 25A. A blood outlet portion is formed by this blood outflow side space 25A and the blood outlet port 28 communicating with the blood outflow side space 25A. When the blood outlet portion has the blood outflow side space 25A, a space through which the blood B that has been transmitted through the filter member 41A flows toward the blood outlet port 28 is secured, and therefore, it is possible to smoothly discharge the blood B.

As shown in FIG. 3, an annular rib 291 is protrusively formed inside the first lid body 22A. A first chamber 221a is defined by the first lid body 22A, the rib 291, and the partition wall 8. This first chamber 221a is a gas outlet chamber through which gas G flows out. The left end opening of each of the hollow fiber membranes 31 of the hollow fiber membrane layer 3A opens to and communicates with the first chamber 221a. In the oxygenator 10, a gas outlet portion is formed by the gas outlet port 27 and the first chamber 221a. On the other hand, an annular rib 292 is also protrusively formed inside the second lid body 23A. A second chamber 231a is defined by the second lid body 23A, the rib 292, and the partition wall 9. This second chamber 231a is a gas inlet chamber through which gas G flows in. The right end opening of each of the hollow fiber membranes 31 of the hollow fiber membrane layer 3A opens to and communicates with the second chamber 231a. In the oxygenator 10, a gas inlet portion is formed by the gas inlet port 26 and the second chamber 231a.

Here, the flow of the blood in the oxygenator 10 of the present embodiment will be described. In this oxygenator 10, the blood B flowing in from the blood inlet port 201 flows into the heat exchange portion 10B after passing through the blood inflow side space 24A and the side holes 243 in order. In the heat exchange portion 10B, heat exchange (heating or cooling) is performed such that the blood B comes into contact with the surface of each of the hollow fiber membranes 31 of the heat exchange portion 10B while flowing through the blood flow paths 33 in a downstream direction. The blood B which has been subjected to heat exchange in this manner flows into the oxygenator portion 10A.

In the oxygenator portion 10A, the blood B flows through the blood flow paths 33 in a further downstream direction. On the other hand, gas (gas containing oxygen) supplied from the gas inlet port 26 is distributed from the second chamber 231a into the flow paths 32 of the hollow fiber membranes 31 of the oxygenator portion 10A, accumulated in the first chamber 221a after flowing through the flow path 32, and is discharged from the gas outlet port 27. The blood B flowing through the blood flow paths 33 comes into contact with the surface of each of the hollow fiber membranes 31 of the oxygenator portion 10A, and gas exchange, that is, addition of oxygen and decarbonation are performed between the blood and the gas G flowing through the flow paths 32.

In a case where air bubbles mixed with the blood B which has been subjected to gas exchange, these air bubbles are captured by the filter member 41A and are prevented from flowing out to the downstream side of the filter member 41A.

The blood B which has been subjected to the heat exchange and the gas exchange as described above in order and from which air bubbles are removed flows out of the blood outlet port 28.

As described above, all the hollow fiber membrane layers 3A and 3B are constituted of a plurality of hollow fiber membranes 31. The hollow fiber membrane layer 3A and the hollow fiber membrane layer 3B have the same hollow fiber membranes 31 even though the application of the hollow fiber membrane layer 3A and the hollow fiber membrane layer 3B are different from each other, and therefore, the hollow fiber membrane layer 3A will be representatively described below.

The inner diameters $\phi d_1$ of the hollow fiber membranes 31 are preferably 50 μm or larger and 700 μm or smaller and more preferably 70 μm or larger and 600 μm or smaller (refer to FIG. 6). The outer diameters $\theta d_2$ of the hollow fiber membranes 31 are preferably 100 μm or larger and 1000 μm or smaller and more preferably 120 μm or larger and 800 μm or smaller (refer to FIG. 6). Furthermore, the ratio $d_1/d_2$ of the inner diameter $\phi d_1$ to the outer diameter $\phi d_2$ is preferably 0.5 or more and 0.9 or less and more preferably 0.6 or more and 0.8 or less. In each of the hollow fiber membranes 31 having such conditions, it is possible to comparatively reduce the pressure loss when the gas G is made to flow in the flow paths 32 which are hollow portions of the hollow fiber membranes 31 while maintaining its strength, and such conditions also contribute to maintaining the winding state of the hollow fiber membranes 31. For example, when the inner diameter $\phi d_1$ is larger than the upper limit value, the thickness of the hollow fiber membranes 31 becomes thin, and the strength of the hollow fiber membranes decreases in accordance with other conditions. In addition, when the inner diameter $\phi d_1$ is smaller than the lower limit value, the pressure loss when the gas G is made to flow in the hollow fiber membranes 31 increases in accordance with other conditions.

In addition, the distance between adjacent hollow fiber membranes 31 is more preferably 1/10 or more and 1/1 or less of the $\phi d_2$.

The method for manufacturing such hollow fiber membranes 31 is not particularly limited, but examples thereof include a method using extrusion molding, and in addition, a method using a stretching method or a solid-liquid phase separation method. It is possible to manufacture the hollow fiber membranes 31 having a predetermined inner diameter $\phi d_1$ and a predetermined outer diameter $\phi d_2$ through this method.

For example, as the constituent material of each of the hollow fiber membranes 31, hydrophobic polymer materials such as polypropylene, polyethylene, polysulfone, polyacrylonitrile, polytetrafluoroethylene, and polymethylpentene are used, a polyolefin resin is preferably used, and polypropylene is more preferably used. The selection of such resin materials contributes to maintaining the winding state of the hollow fiber membranes 31 and also to cost reduction during the manufacture of the hollow fiber membranes.

The hollow fiber membrane layer 3A is manufactured by winding such a plurality of hollow fiber membranes 31 around a columnar core as follows.

FIGS. 7A, 7B, 8A, and 8B are views showing a state in which the hollow fiber membrane layer is manufactured, where (a) is a perspective view and (b) is a development view.

As shown in FIGS. 7A, 7B, 8A, and 8B, a hollow fiber membrane 31 is reciprocated in a central axis O direction while being wound around a central axis O of the first cylindrical member 241 (cylindrical body). At this time, the hollow fiber membrane 31 starts winding from a left side starting point 311 of the central axis O direction and goes to the right side. On the right side, the hollow fiber membrane 31 is folded back at a folding point (folded-back portion) 312. Thereafter, the hollow fiber membrane 31 returns to the left side again and reaches an ending point 313. For example, in the winding state shown in FIG. 7, the hollow fiber membrane 31 is wound in the order of arrows i→ii→iii→iv→v. Then, during one reciprocation, as shown in FIGS. 7A and 7B, the hollow fiber membrane 31 is wound at a predetermined number of turns X. In the winding state shown in FIGS. 7A and 7B, X=1, and the hollow fiber membrane 31 makes one around the central axis O while making one reciprocation. In addition, in the winding state shown in FIGS. 8A and 8B, the hollow fiber membrane 31 is wound in the order of arrows i→ii→iii→iv→v→vi→vii. Then, during one reciprocation, as shown in FIGS. 8A and 8B, the hollow fiber membrane 31 makes two turns around the central axis O.

Thus, the hollow fiber membrane layer 3A includes the hollow fiber membranes 31 inclined with respect to the central axis and wound around the central axis.

As shown in FIG. 9, the hollow fiber membrane 31 has a barrier layer 5 and a heat conductive layer 6 and the layers are preferably laminated concentrically in this order from inside to outside.

The barrier layer 5 has a function of preventing hydrogen peroxide in the heat medium from permeating to the outside.

Here, in such an oxygenator 10, a liquid containing hydrogen peroxide solution is used as a heat medium H (hereinafter, simply referred to as "heat medium") in the hollow fiber membrane layer 3B. Accordingly, inside of the hollow fiber membranes 31 can be sterilized. However, depending on the constituent material of the hollow fiber membrane 31, hydrogen peroxide may permeate from the heat medium, and as a result, hydrogen peroxide may be mixed in the blood. According to the present invention, such a problem can be solved. Hereinafter, the configuration of the hollow fiber membranes 31 will be described in detail.

When viewing the hollow fiber membrane 31 as a whole, when the hollow fiber membrane 31 has an oxygen permeability coefficient of 6 cc·cm/m²·24 h/atm or less at 25° C., it is possible to prevent hydrogen peroxide from being mixed with the blood outside the hollow fiber membranes 31. Note that, "oxygen permeability coefficient" in the present specification means a numerical value obtained by converting the permeation amount [cc·cm/m²] of oxygen per unit area in the hollow fiber membrane 31 into 1 atm for 24 hours.

In addition, in a case where the hollow fiber membrane 31 has an oxygen permeability coefficient of 3.8 cc·cm/m²·24 h/atm or less at 25° C., and therefore, the above-described effects can be more reliably exhibited and can be exhibited over a long period of time.

In addition, it is preferable that the hollow fiber membrane 31 has an oxygen permeability coefficient of 0.1 cc·cm/m²·24 h/atm or more at 25° C. In a case where the oxygen permeability coefficient is less than 0.1 cc·cm/m$^2$·24 h/atm, selection of the material of the barrier layer 5 becomes difficult.

Note that, if the oxygen permeability coefficient exceeds the above numerical range, the permeation amount of hydrogen peroxide may be increased and the concentration of hydrogen peroxide in the blood may be increased.

In addition, the present inventors found that the correlation coefficient between the oxygen permeability coefficient and the hydrogen peroxide permeability coefficient is 0.99, and these are correlated. Accordingly, even when the hollow fiber membrane 31 is manufactured based on any one of the hydrogen peroxide permeability coefficient and the oxygen permeability coefficient, it is highly probable that the other coefficient is necessarily in the above numerical range.

In addition, the thickness 15 of the barrier layer 5 is preferably 1 μm or more and 60 μm or less, and more preferably 30 μm or more and 50 μm or less. When the barrier layer 5 is too thin, the oxygen permeability coefficient tends to be low. When the barrier layer 5 is too thick, the outer diameter of the hollow fiber membrane 31 tends to increase in the case where the inner diameter of the hollow fiber membrane 31 is sufficiently ensured, and as a result, the blood filling amount may be increased and the burden on the user may be increased.

The barrier layer 5 is mainly made of a crystalline resin material. In the present specification, "crystalline resin material" refers to a resin having a high ratio of the amount of crystalline regions in which molecular chains are regularly arranged. Examples thereof include polyethylene (PE), polypropylene (PP), polyamide (PA), polyacetal (POM), polybutylene terephthalate (PBT), polyethylene terephthalate (PET), syndiotactic polystyrene (SPS), polyphenylene sulfide (PPS), polyether ether ketone (PEEK), liquid crystal polymer (LCP), and polyether nitrile (PEN), and among these, aliphatic polyamide is preferably used.

When the number of carbon atoms in the amide groups of the aliphatic polyamide molecule is N and the number of carbon atoms in the methylene groups of the aliphatic polyamide molecule is n, n/N of the aliphatic polyamide is preferably 9 or more, and for example, at least one of polyamide 11, polyamide 12, polyamide 10-10, and polyamide 10-12 is preferably used. Accordingly, the oxygen permeability coefficient can be made sufficiently low. In addition, by using aliphatic polyamide in which n/N is 9 or more, the water absorption rate of the barrier layer 5 can be made 2% or lower. Accordingly, high hydrophobicity can be exhibited with respect to a heat medium containing hydrogen peroxide solution. Since hydrogen peroxide has a relatively high affinity with respect to water, hydrogen peroxide easily permeates if the water absorption rate is relatively high, but by setting the water absorption rate of the barrier layer 5 to be 2% or less, excessive permeation of hydrogen peroxide can be prevented.

Here, in order to lower the oxygen permeability coefficient, it is conceivable to increase the thickness of the barrier layer 5, but if the thickness of the barrier layer 5 is too thick, the oxygen permeability coefficient may be lowered, but the thermal conductivity is lowered. As a result, there is a concern that the function of the hollow fiber membrane layer 3B as a heat exchanger may deteriorate. From such a viewpoint, in the hollow fiber membranes 31, the heat conductive layer 6 having a thermal conductivity higher than that of the barrier layer 5 is provided outside the barrier layer 5. The thermal conductivity can be compensated by the heat conductive layer 6 while the thickness of the barrier layer 5 can be sufficiently secured. Accordingly, it is possible to prevent the thermal conductivity being lowered while maintaining a high hydrogen peroxide permeability coefficient.

The thermal conductivity of the heat conductive layer 6 is preferably 0.2 W/m·K or higher and 0.60 W/m·K or lower, and more preferably 0.3 W/m·K or higher and 0.55 W/m·K or lower. Accordingly, the above-described effects can be more reliably exhibited.

The material of such a heat conductive layer 6 is not particularly limited as long as it exhibits the above-described effects. For example, at least one selected from the group including polyolefin, polyamide such as nylon 66, polyurethane, polyester such as polyethylene terephthalate, polybutylene terephthalate, and polycyclohexane terephthalate, and a fluorine-based resin such as polytetrafluoroethylene and ethylene-tetrafluoroethylene copolymer can be used. Among these, high density polyethylene is preferably used. Accordingly, the above-described effects can be reliably exhibited.

The thickness $T_6$ of the heat conductive layer 6 is preferably 10 μm or more and 60 μm or lower, and more preferably 20 μm or more and 50 μm or lower. Accordingly, the thermal conductivity of the hollow fiber membranes 31 can be sufficiently enhanced.

As described above, according to the present invention, the barrier layer 5 has an oxygen permeability coefficient of 6 cc·cm/m$^2$·24 h/atm or less at 25° C., so that hydrogen peroxide can be prevented from permeating the barrier layer 5, and the concentration of hydrogen peroxide in the blood flowing outside the hollow fiber membranes 31 can be prevented from increasing.

Second Embodiment

Figure 11:
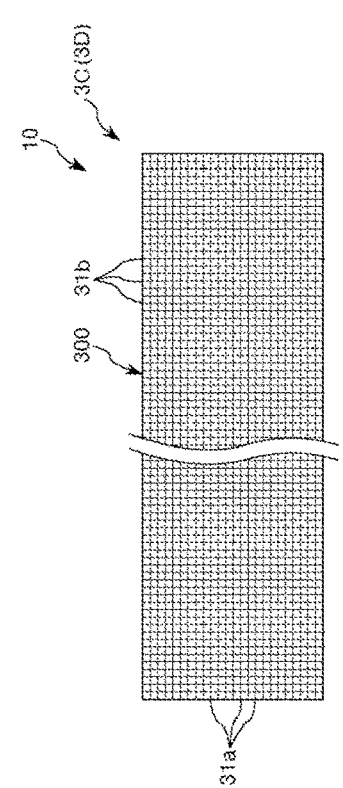
FIG. 11 is a plan view showing a hollow fiber membrane sheet before becoming a hollow fiber membrane layer of a heat exchanger (second embodiment) of the present invention.
Figure 12:
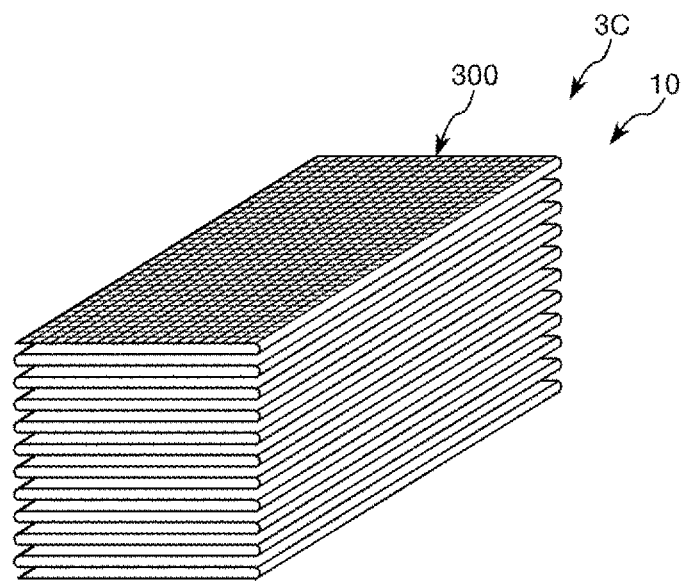
FIG. 12 is a perspective view of a hollow fiber membrane layer formed by folding the hollow fiber membrane sheet shown in FIG. 11.

FIG. 11 is a plan view showing a hollow fiber membrane sheet before becoming a hollow fiber membrane layer of a heat exchanger (second embodiment) of the present invention. FIG. 12 is a perspective view of a hollow fiber membrane layer formed by folding the hollow fiber membrane sheet shown in FIG. 11.

Hereinafter, a second embodiment of a heat exchanger of the present invention will be described while referring to the drawings. However, the difference from the above-described embodiment will be mainly described and the description of the same matter will not be repeated.

The present embodiment is the same as the first embodiment except that the configuration of the hollow fiber membrane layer is different from that in the first embodiment. A hollow fiber membrane layer 3C in the oxygenator 10 of the present embodiment is constituted of a hollow fiber membrane sheet 300 shown in FIG. 11.

The hollow fiber membrane sheet 300 is a sheet which has warp strings 31a composed of the plurality of hollow fiber membranes 31 and weft strings 31b composed of the plurality of hollow fiber membranes 31, and is formed by braiding the warp strings and the weft strings.

As shown in FIG. 12, the hollow fiber membrane sheet 300 is alternately folded in the surface direction to form the hollow fiber membrane layer 3C having a prismatic outer shape.

The same effects as that of the first embodiment can be also obtained by such a hollow fiber membrane layer 3C.

Third Embodiment

Figure 13:
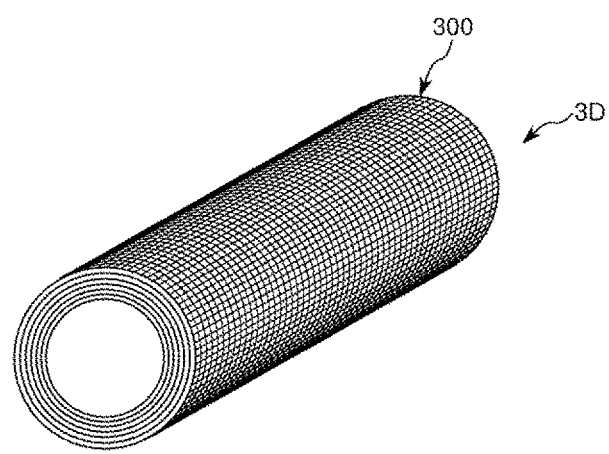
FIG. 13 is a perspective view of a hollow fiber membrane layer provided in a heat exchanger (third embodiment) of the present invention.

FIG. 13 is a perspective view of a hollow fiber membrane layer provided in a heat exchanger (third embodiment) of the present invention.

Hereinafter, a third embodiment of a heat exchanger of the present invention will be described while referring to the drawing. However, the difference from the above-described embodiment will be mainly described and the description of the same matter will not be repeated. The present embodiment is the same as the first embodiment except that the configuration of the hollow fiber membrane layer is different from that in the first embodiment.

As shown in FIG. 13, a hollow fiber membrane layer 3D is molded into a cylindrical shape by winding the hollow fiber membrane sheet 300 shown in FIG. 11 in a roll shape a plurality of times.

The same effects as the first embodiment and the second embodiment can also be achieved with such a present embodiment.

Although the heat exchanger and the oxygenator of the present invention have been described above with reference to the illustrated embodiments, the present invention is not limited thereto.

In addition, each of the hollow fiber membranes constituting the hollow fiber membrane layer of the oxygenator portion and each of the hollow fiber membranes constituting the hollow fiber membrane layer of the heat exchange portion were the same as each other in the embodiments, but the present invention is not limited thereto. For example, one (former) hollow fiber membrane side may be thinner than the other (latter) hollow fiber membrane side, or both hollow fiber membrane sides may be formed of materials different from each other.

In addition, in the oxygenator portion and the heat exchange portion, the heat exchange portion is disposed inside and the oxygenator portion is disposed outside in the embodiments. However, the present invention is not limited thereto, and the oxygenator portion may be disposed inside and the heat exchange portion may be disposed outside. In this case, blood flows down from the outside to the inside.

EXAMPLES

Hereinafter, specific examples of the present invention will be described. Note that, the present invention is not limited to this.

1. Production of Heat Exchanger (Example 1)

A heat exchanger as shown in FIGS. 1 to 5 was produced. In this heat exchanger, the hollow fiber membrane is made of PET having characteristics shown in Table 1, and has an inner diameter of 480 μm and an outer diameter of 600 μm.

Example 2

A heat exchanger of Example 2 was made in the same manner as Example 1 except that the constituent material of the hollow fiber membrane was changed to polyamide 12 (Daicel-Evonik Ltd., "DAIAMID") having characteristics as shown in Table 1.

Comparative Example 1

A heat exchanger of Comparative Example 1 was obtained in the same manner as Example 1 except that the constituent material of the hollow fiber membrane was changed to polyurethane having characteristics as shown in Table 1.

Comparative Example 2

A heat exchanger of Comparative Example 2 was obtained in the same manner as the Example 1 except that the constituent material of the hollow fiber membrane was changed to polyamide elastomer (TOYOBO CO., LTD, "PELPRENE") having characteristics as shown in Table 1.

2. Evaluation

Each of the above-described examples and each of the above-described comparative examples were evaluated by the following methods.

Figure 10:
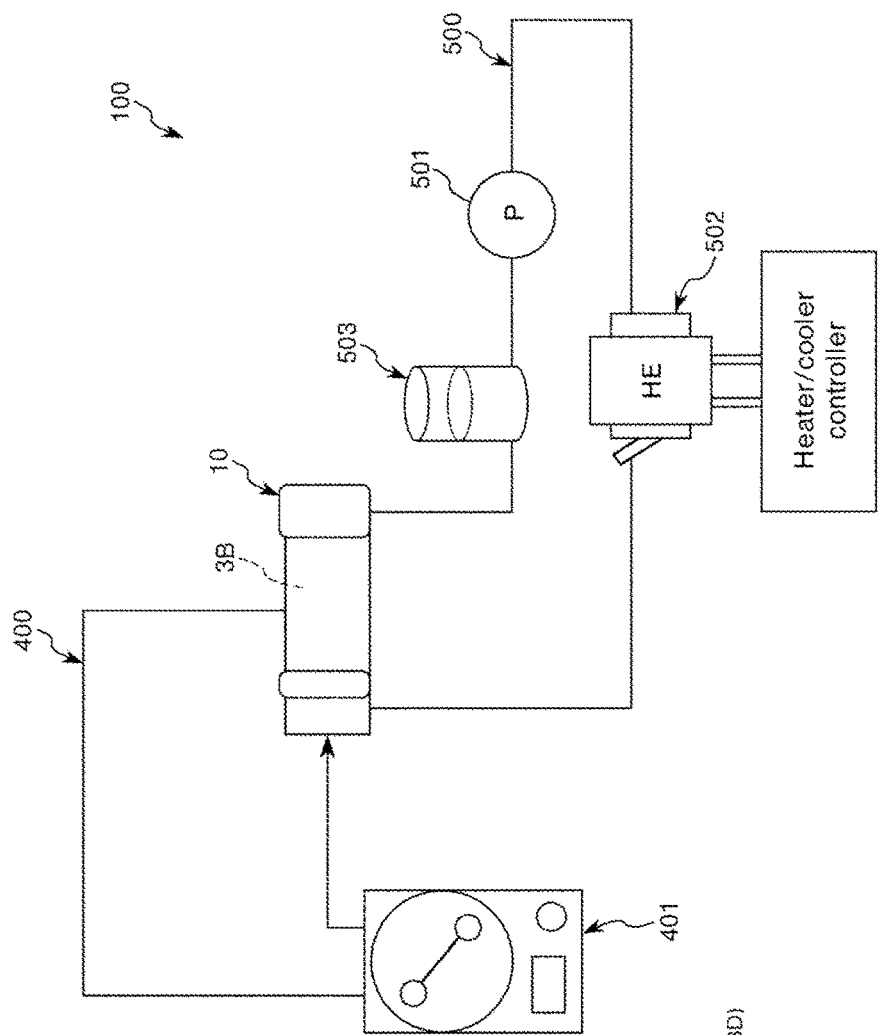
FIG. 10 is a schematic view showing a state of conducting an experiment for obtaining a hydrogen peroxide permeability coefficient in the hollow fiber membrane provided in the heat exchanger shown in FIG. 1.

FIG. 10 is a schematic view showing a state of conducting an experiment for obtaining a hydrogen peroxide permeability coefficient in the hollow fiber membrane provided in the heat exchanger shown in FIG. 1. This circulation system 100 shown in FIG. 10 has a physiological saline supply line 400, a heat medium supply line 500, and the oxygenator 10.

The physiological saline supply line 400 has a pump 401 provided in the middle to supply and circulate the physiological saline to the outside of the hollow fiber membranes 31 of the hollow fiber membrane layer 3B of the oxygenator 10. In the present embodiment, the physiological saline is regarded as blood to conduct an experiment.

The heat medium supply line 500 has a pump 501 provided in the middle, a temperature control unit 502 for adjusting the temperature of the heat medium, and a heat medium storage portion 503. The heat medium supply line 500 supplies and circulates the heat medium inside the hollow fiber membranes 31 of the hollow fiber membrane layer 3B of the oxygenator 10.

In the circulation system 100, a heat medium circulating inside the hollow fiber membranes 31 performs heat exchange on the physiological saline circulating outside the hollow fiber membranes 31 through the hollow fiber membranes 31.

In addition, in the physiological saline supply line 400, the concentration of physiological saline was set to 0.9% [g/L], maintained at 29.5° C. or higher and 30.5° C., and made to flow down at a flow rate of 4 L/min.

In addition, in the heat medium supply line 500, the concentration of hydrogen peroxide of the heat medium was set to 0.033% [v/v], maintained at 29.5° C. or higher and 30.5° C., and made to flow down at a flow rate of 10 L/min.

Under such conditions, the permeation amount of hydrogen peroxide in physiological saline was measured by the experiment under the conditions described below.

<Hydrogen Peroxide Permeation Amount 1>

Using the circulation system 100 shown in FIG. 10, the concentration of hydrogen peroxide of heat medium was set to 0.033% [v/v], maintained at 29.5° C. or higher and 30.5° C., and made to flow down at a flow rate of 10 L/min for 3 hours.

<Hydrogen Peroxide Permeation Amount 2>

Using the circulation system 100 shown in FIG. 10, the concentration of hydrogen peroxide of heat medium was set to 0.033% [v/v], maintained at 29.5° C. or higher and 30.5° C., and made to flow down at a flow rate of 10 L/min for 6 hours.

<Environmental Stress Crack>

The heat exchangers were immersed in a high level disinfectant hydrogen peroxide solution (6% content), a medium level disinfectant (containing 1% sodium hypochlorite), and a low level disinfectant (containing benzalkonium chloride solution 0.2%) for 24 hours each. The surface of the hollow fiber membranes was then observed with a microscope when it was observed whether the surface was cracked or liquid leakage occurred. The results were evaluated based on the following evaluation criteria.

A: There were no cracks or liquid leakage.
B: No liquid leakage occurred, but some cracks were observed.
C: There were a crack and liquid leakage.
The evaluation results are shown in Table 1.

TABLE 1

|  | Example 1 | Example 2 | Comparative Example 1 | Comparative Example 2 |
|---|---|---|---|---|
| Outer diameter [μm] of hollow fiber membrane | 600 | 550 | 575 | 550 |
| Inner diameter [μm] of hollow fiber membrane | 480 | 450 | 465 | 450 |
| Membrane area [m$^2$] | 0.44 | 0.45 | 0.4 | 0.45 |
| Oxygen permeability coefficient [cc·cm/m$^2$·24 h/atm] | 0.108 | 2.75 | 6.75 | 85 |
| Hydrogen Peroxide Permeation Amount 1 [mg] | 0.02 | 0.36 | 0.69 | 2.64 |
| Hydrogen Peroxide Permeation Amount 2 [mg] | 0.05 | 0.69 | 1.39 | 4.73 |
| Environmental Stress Crack | B | A | A | A |

As clear from Table 1, the heat exchangers of Examples 1 and 2 have lower oxygen permeability coefficients and hydrogen peroxide permeation amounts than the heat exchangers of Comparative Examples 1 and 2, and have been demonstrated to prevent an increase in the concentration of hydrogen peroxide in blood.

According to the present invention, it has been demonstrated that, when the oxygen permeability coefficient of the hollow fiber membranes 31 is set to 6 cc·cm/m$^2$24 h/atm or less, a heat exchanger having a higher barrier property to hydrogen peroxide solution than that of the existing hollow fiber membranes for artificial heart lungs can be obtained.

In addition, in the above description, the present invention has been described by way of preferred embodiments, but the present invention is not limited to the above embodiments, and it goes without saying that various modifications can be made without departing from the scope of the present invention.

The heat exchanger of the present invention is a heat exchanger including a hollow fiber membrane layer having a plurality of hollow fiber membranes. Each of the hollow fiber membranes has a barrier layer having a hydrogen peroxide barrier property, and the barrier layer has an oxygen permeability coefficient of 6 cc·cm/m$^2$·24 h/atm or less at 25° C. According to the present invention, since the barrier layer provided in the hollow fiber membrane has an oxygen permeability coefficient of 6 cc·cm/m$^2$·24 h/atm or less at 25° C., it is possible to prevent hydrogen peroxide from permeating the hollow fiber membranes even in a case where a liquid containing hydrogen peroxide solution is used as a heat medium. Therefore, it is possible to prevent the concentration of hydrogen peroxide in the blood from increasing.

What is claimed is:

1. A heat exchanger for a blood circulation circuit, comprising:
    a hollow fiber membrane layer having a plurality of hollow fiber membranes; and
    a housing receiving the hollow fiber membrane layer to define a first flow path including hollow portions of the hollow fiber membranes and to define a second flow path in a gap between the hollow fiber membranes, wherein one of the flow paths conveys blood and the other flow path conveys a heat medium;
    wherein each of the hollow fiber membranes is comprised of a plurality of laminated layers including a barrier layer having a hydrogen peroxide barrier property; and
    wherein the barrier layer has an oxygen permeability coefficient of 6 cc·cm/m$^2$·24 h/atm or less at 25° C.

2. The heat exchanger according to claim 1:
    wherein the barrier layer is comprised of a crystalline resin material.

3. The heat exchanger according to claim 2:
    wherein the crystalline resin material includes an aliphatic polyamide.

4. The heat exchanger according to claim 3:
    wherein the aliphatic polyamide is comprised of at least one of polyamide 11, polyamide 12, polyamide 10-10, and polyamide 10-12.

5. The heat exchanger according to claim 3:
    wherein the number of carbon atoms in amide groups of a molecule of the aliphatic polyamide is N, and wherein the number of carbon atoms in methylene groups of the aliphatic polyamide is n; and
    wherein n/N is 9 or larger.

6. The heat exchanger according to claim 2:
    wherein the plurality of layers further includes a heat conductive layer having a thermal conductivity higher than a thermal conductivity of the barrier layer.

7. The heat exchanger according to claim 6:
    wherein the heat conductive layer has a thermal conductivity between 0.2 W/m·K and 0.60 W/m·K.

8. The heat exchanger according to claim 1:
    wherein the hollow fiber membrane layer has a shape of a cylindrical body and has the hollow fiber membranes wound around a central axis of the cylindrical body and inclined with respect to the central axis of the cylindrical body.

9. The heat exchanger according to claim 1:
    wherein the hollow fiber membrane layer includes a formed sheet material having the plurality of hollow fiber membranes braided.

10. The heat exchanger according to claim 1:
    wherein the heat medium is comprised of a hydrogen peroxide solution which is circulated through the first flow path, and wherein the blood is circulated through the second flow path.

11. A heat exchanger for a blood circulation circuit, comprising:
    a hollow fiber membrane layer having a plurality of hollow fiber membranes; and
    a housing receiving the hollow fiber membrane layer to define a first flow path including hollow portions of the hollow fiber membranes and to define a second flow path in a gap between the hollow fiber membranes, wherein one of the flow paths conveys blood and the other flow path conveys a heat medium;
    wherein the hollow fiber membranes are comprised of a plurality of laminated layers in a thickness direction of the hollow fiber membranes; and
    wherein one of the layers is a barrier layer having a hydrogen peroxide barrier property with an oxygen permeability coefficient of 6 cc·cm/m$^2$·24 h/atm or less at 25° C.

12. An oxygenator for a blood circulation circuit, comprising:
    a hollow fiber membrane layer having a plurality of hollow fiber membranes; and a housing receiving the hollow fiber membrane layer to define a first flow path including hollow portions of the hollow fiber membranes and to define a second flow path in a gap between the hollow fiber membranes, wherein one of the flow paths conveys blood and the other flow path conveys a heat medium;

wherein each of the hollow fiber membranes is comprised of a plurality of laminated layers including a barrier layer having a hydrogen peroxide barrier property; and wherein the barrier layer has an oxygen permeability coefficient of 6 cc·cm/m²·24 h/atm or less at 25° C.

13. The oxygenator according to claim 12:

wherein the barrier layer is comprised of a crystalline resin material.

14. The oxygenator according to claim 13:

wherein the crystalline resin material includes an aliphatic polyamide.

15. The oxygenator according to claim 14:

wherein the aliphatic polyamide is comprised of at least one of polyamide 11, polyamide 12, polyamide 10-10, and polyamide 10-12.

16. The oxygenator according to claim 14:

wherein the number of carbon atoms in amide groups of a molecule of the aliphatic polyamide is N, and wherein the number of carbon atoms in methylene groups of the aliphatic polyamide is n; and wherein n/N is 9 or larger.

17. The oxygenator according to claim 13:

wherein the plurality of layers further includes a heat conductive layer having a thermal conductivity higher than a thermal conductivity of the barrier layer.

18. The oxygenator according to claim 17:

wherein the heat conductive layer has a thermal conductivity between 0.2 W/m·K and 0.60 W/m·K.

19. The oxygenator according to claim 12:

wherein the hollow fiber membrane layer has a shape of a cylindrical body and has the hollow fiber membranes wound around a central axis of the cylindrical body and inclined with respect to the central axis of the cylindrical body.

20. The oxygenator according to claim 12:

wherein the hollow fiber membrane layer includes a formed sheet material having the plurality of hollow fiber membranes braided.

* * * * *